United States Patent
Kohno et al.

(10) Patent No.: US 6,240,159 B1
(45) Date of Patent: May 29, 2001

(54) FLUORESCENT X-RAY ANALYZER WITH PATH SWITCHING DEVICE

(75) Inventors: Hisayuki Kohno; Shirou Higaki, both of Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 09/456,480

(22) Filed: Dec. 7, 1999

(30) Foreign Application Priority Data

Dec. 28, 1998 (JP) .................................................. 10-372438

(51) Int. Cl.[7] .................................................. G01N 23/223
(52) U.S. Cl. .................................................. 378/45; 378/46
(58) Field of Search .................................. 378/45, 44, 46, 378/49, 50, 70

(56) References Cited

U.S. PATENT DOCUMENTS 4,916,720 * 4/1990 Yamammoto et al. ................ 378/81
4,959,848 * 9/1990 Parobek .................................. 378/46
5,406,608 * 4/1995 Yellepeddi et al. .................... 378/46

* cited by examiner

Primary Examiner—Robert H. Kim
Assistant Examiner—Irakli Kiknadze
(74) Attorney, Agent, or Firm—Sughrue, Mion, Zinn, Macpeak & Seas, PLLC

(57) ABSTRACT

A fluorescent X-ray analyzer has at least three optical detection paths along which the secondary fluorescent X-ray to be analyzed travels selectively and includes a monochromator (6) carried by a first spindle (14) having a longitudinal axis (O) passing in touch with a light receiving surface of the monochromator (6). A first detector (8A) for measuring the intensity of at least a portion of the secondary X-ray (7) monochromatized by the monochromator (6) while allowing the remaining portion of the secondary X-ray (7) to pass therethrough, and a light receiving slit member (11) for passing the secondary X-ray (7) monochromatized by the monochromator (6) therethrough are carried by a second spindle (17) in side-by-side relation in a circumferential direction. A third spindle (20) is utilized separate from the second spindle (17) for carrying a second detector (8B) for measuring the intensity of the secondary X-ray (7) having passed through the first detector (8A) or the light receiving slit member (11).

10 Claims, 4 Drawing Sheets

FLUORESCENT X-RAY ANALYZER WITH PATH SWITCHING DEVICE

BACKGROUND OF THE INVENTION

1. Field of the Invention

The present invention generally relates to a so-called scanning fluorescent X-ray analyzer and, more particularly, to a path switching device used in association with the scanning fluorescent X-ray analyzer for selecting one of three or more optical detection paths along which respective beams to be analyzer travel.

2. Description of the Prior Art

Hitherto, the fluorescent X-ray analyzer of a so-called wavelength divergence type is, as shown in FIG. 4, so designed as to irradiate a sample piece 1 with a primary X-ray 3, generated from an X-ray source 4 such as, for example, an X-ray tube, to cause the sample piece 1 to generate a fluorescent X-ray (secondary X-ray) 5 which is, after having been passed through a divergent slit 13, subsequently monochromatized by a monochromator 6 to provide a monochromatized fluorescent X-ray 7 that is finally detected by a detector 8. In this type of the fluorescent X-ray analyzer, the detector 8 makes use of two counters, i.e., a gas-flow proportional counter tube (hereinafter referred to as "F-PC") 8A for detection of the low-energy fluorescent X-rays and a scintillation counter (hereinafter referred to as "SC") 8B for detection of the high-energy fluorescent X-rays. A light receiving slit 11A is disposed in front of the SC 8B, whereas the F-PC 8A has a light receiving slit (not shown) built therein at a front thereof.

According to the prior art, when the high-energy fluorescent X-ray 7 is desired to be measured, in order to vary the wavelength of the fluorescent X-ray 7 incident upon the SC 8B, the use has been made of a linkage means (not shown) for continuously associating the monochromator 6 with both of the light receiving slit 11A and the SC 8B so that fluorescent X-rays 5 generated from various elements contained in the sample piece 1 can be monochromatized according to respective wavelengths with the intensity thereof subsequently measured.

In other words, when the fluorescent X-ray 5 impinges upon the monochromator 6 at an angle of incidence θ, an extension 9 of the path of travel of the fluorescent X-ray 5 having passed through the divergent slit 13 and the fluorescent X-ray 7 that has been monochromatized by the monochromator 6 form an angle of diffraction 2θ which is twice the angle of incidence θ. However, the linkage means referred to above serves to vary the angle of diffraction 2θ to vary the wavelength of the monochromatized fluorescent X-ray 7 so that the monochromatized fluorescent X-ray 7 can enter the SC 8B through the light receiving slit 11A. In other words, the linkage means is operable to rotate the monochromator 6 about a pivot axis O lying perpendicular to the plane of a sheet of the drawing of FIG. 4 and passing across the center of a light receiving surface of the monochromator 6, and also to turn, in synchronism with rotation of the monochromator 6, both of the light receiving slit 11A and the SC 8B about the pivot axis O along a circular path 12A through an angle that is equal to twice the angle of rotation of the monochromator 6.

More specifically, a θ spindle (not shown) having the monochromator 6 mounted thereon with the pivot axis O passing through the light receiving surface of the monochromator 6 and coaxially occupied by the θ spindle is rotated to cause a 2θ spindle (not shown), on which the F-PC 8A and both of the light receiving slit 11A and the SC 8B are mounted in side-by-side relation in a direction conforming to the direction of turn thereof, to be turned an angle equal to twice the angle of rotation of the θ spindle.

On the other hand, where the intensity of the low-energy fluorescent X-ray 7 is desired to be measured, the angle at which the monochromator 6 is fitted to the θ spindle is turned to a predetermined angle so that the fluorescent X-ray 7 monochromatized by the monochromator 6 can enter the F-PC 8A. (This also applies where the analyzer includes a plurality of monochromators and one of the monochromators is selectively utilized.) The linkage means operates in a manner similar to that described above.

Thus, in this prior art fluorescent X-ray analyzer, a detection path extending from the monochromator 6 to the SC 8B via the light receiving slit 11A and a detection path extending from the monochromator 6 to the F-PC 8A can be selectively utilized one at a time.

With the prior art fluorescent X-ray analyzer, it has been found that since the SC 8B is fixed in position at a location rearwardly of the light receiving slit 11A and mounted on the 2θ spindle, it is impossible to position the SC 8B at a location rearwardly of the F-PC 8A. Accordingly, a third detection path can in no way be selected, which would be necessitated where even though the fluorescent X-ray 7 has been received by the F-PC 8A, a portion of the fluorescent X-ray 7 having passed beyond the F-PC 8A without being measured as to its intensity completely is to be measured by the SC 8B so that the intensity of the fluorescent X-ray 7 as a whole can be accurately measured by summing the intensity of the fluorescent X-ray 7 measured by the F-PC 8A and the intensity of the remaining portion of the fluorescent X-ray 7 measured by the SC 8B together.

SUMMARY OF THE INVENTION

Accordingly, the present invention has been devised with a view to substantially eliminating the above discussed problems inherent in the prior art fluorescent X-ray analyzer of the type discussed hereinabove and is intended to enable the scanning fluorescent X-ray analyzer to select one of three or more optical detection paths along which respective fluorescent X-rays to be analyzer travel.

In order to accomplish this object of the present invention, there is provided a fluorescent X-ray analyzer comprising a sample bench for support thereon of a sample piece, an X-ray source for radiating a primary X-ray towards the sample piece on the sample bench, and a monochromator for monochromatizing a secondary X-ray emitted from the sample piece. A first detector is utilized for measuring the intensity of at least a portion of the secondary X-ray monochromatized by the monochromator while allowing the remaining portion of the secondary X-ray to pass therethrough. The fluorescent X-ray analyzer also comprises a light receiving slit member operable to pass therethrough the secondary X-ray which has been monochromatized by the monochromator, and a second detector for measuring the intensity of the secondary X-ray which has been passed through the first detector or the light receiving slit member.

The fluorescent X-ray analyzer furthermore comprises a first spindle having a longitudinal axis and carrying the monochromator with the longitudinal axis thereof passing in touch with a light receiving surface of the monochromator; a first drive mechanism for driving the first spindle; a second spindle having a longitudinal axis coaxial and common with the longitudinal axis of the first spindle and carrying the first detector and the light receiving slit member in a side-by-side fashion; a second drive mechanism for driving the second spindle; a third spindle having a longitudinal axis coaxial and common with the longitudinal axis of the first spindle and carrying the second detector; and a third drive mechanism for driving the third spindle. A control means is utilized to control the first and second drive mechanisms to vary a wavelength of the secondary X-ray incident upon the first detector or the light receiving slit member and for controlling the third drive mechanism to cause the secondary X-ray, having passed through the first detector or the light receiving member, to impinge upon the second detector.

According to the present invention, since the second detector is carried by the third spindle which is different and independent from the second spindle by which the first detector and the light receiving slit member are carried in the form as arranged in side-by-side relation with each other in the circumferential direction, one of at least three optical detection paths, i.e., a first optical detection path extending from the monochromator to the second detector through the light receiving slit member, a second optical detection path extending from the monochromator to the first detector and a third optical detection path extending from the monochromator to the second detector through the first detector, can be selected. Accordingly, since a combination of the light receiving slit member and the detector optimum to the analysis can be selected, the sensitivity of analysis, the analytical precision and the analytical accuracy can advantageously be increased.

The third drive mechanism referred to above may be mounted on the second spindle. Also, this third drive mechanism may comprise a cranking member rotatable about an axis fixed relative to the second spindle; and a rocking arm having one of opposite ends thereof fixed to the third spindle and capable of being rocked about the longitudinal axis of the third spindle by the cranking member. In this case, the second detector is disposed at a location spaced from such one of the opposite ends of the rocking arm. According to these features, the structure can advantageously be simplified.

The first drive mechanism preferably comprises a stepper motor having a drive shaft, a worm gear mounted on the drive shaft of the stepper motor for rotation together therewith, and a helical gear fixedly mounted on the first spindle and drivingly meshed with the worm gear.

Also, the second drive mechanism preferably comprises a stepper motor having a drive shaft, a worm gear mounted on the drive shaft of the stepper motor for rotation together therewith, and a helical gear fixedly mounted on the second spindle and drivingly meshed with the worm gear.

The third drive mechanism preferably comprises a stepper motor having a drive shaft, a worm gear mounted on the drive shaft of the stepper motor for rotation together therewith, a helical gear drivingly meshed with the worm gear, and the arm having a slot defined therein, in which slot a connecting pin fixed to the helical gear so as to protrude laterally outwardly from the helical gear is loosely engaged. In this case, the cranking member is constituted by the helical gear and the connecting pin.

The first detector which can be employed in the practice of the present invention may be either a gas-flow proportional counter tube or a sealed proportional counter tube. Similarly, the second detector which can be employed in the practice of the present invention may be either a scintillation counter or a sealed proportional counter tube.

Preferably, the light receiving slit member comprises a plurality of light receiving slit elements. According to this feature, since in the optical detection path extending from the monochromator to the second detector through the light receiving slit member, the optical detection paths having the different light receiving slit elements can be selected one at a time, the number of the optical detection paths that can be selected can be increased to at least four.

BRIEF DESCRIPTION OF THE DRAWINGS

In any event, the present invention will become more clearly understood from the following description of a preferred embodiment thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENT

Figure 1:
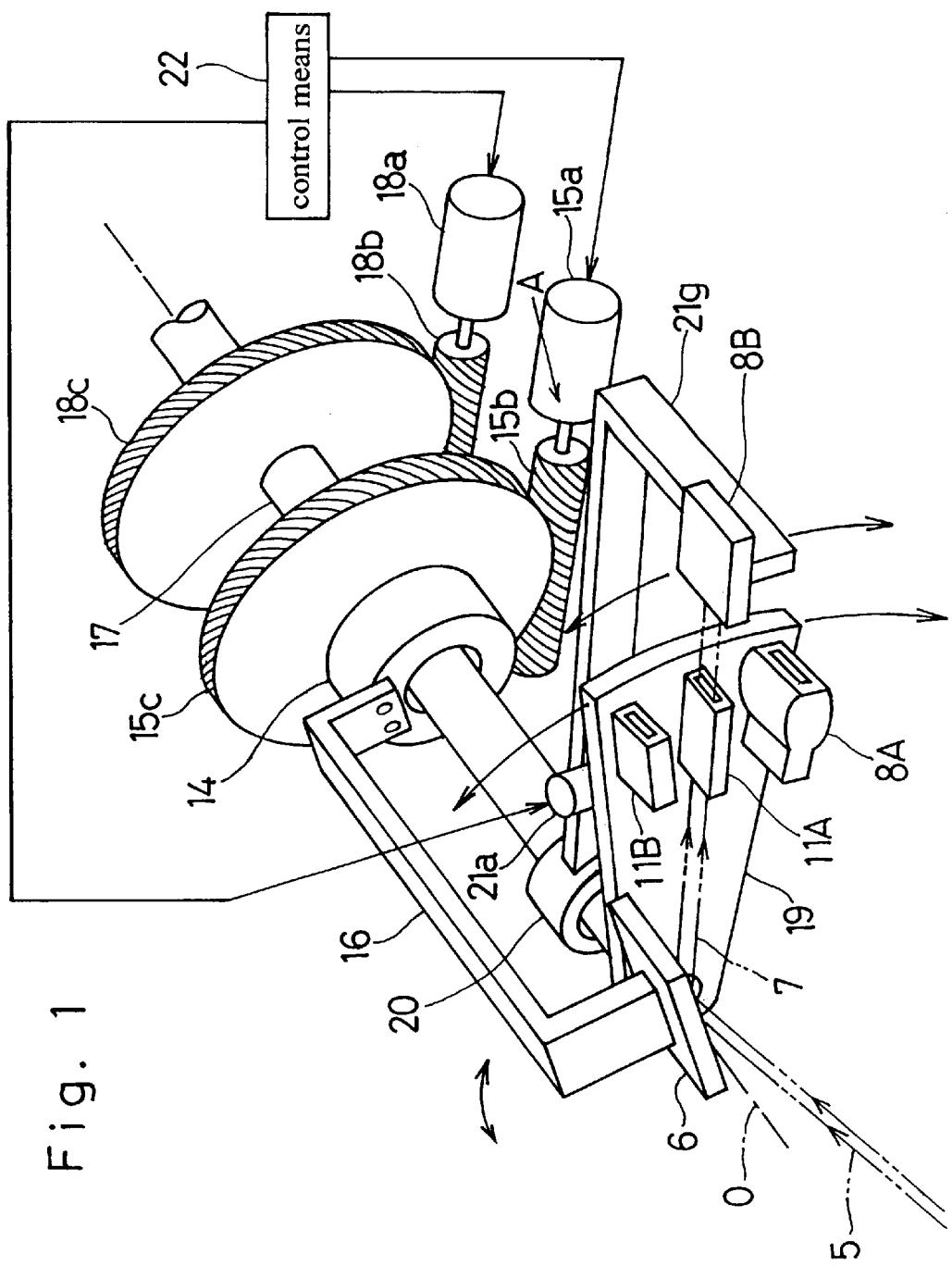
FIG. 1 is a perspective view showing a path switching device employed in a fluorescent X-ray analyzer according to a preferred embodiment of the present invention.

Referring to the accompanying drawings, particularly to FIGS. 1 to 3, a path switching device employed in the fluorescent X-ray analyzer for selecting one of three or more optical detection paths will be described. As schematically shown in a front view in FIG. 3, the fluorescent X-ray analyzer embodying the present invention comprises a sample table 2 for the support thereon of a sample piece 1 to be analyzed, an X-ray source 4 for emitting a primary X-ray 3 towards the sample piece 1 on the sample table 2, and a monochromator 6 for monochromatizing a secondary X-ray 5 such as, for example, a fluorescent X-ray generated from the sample piece 1.

The fluorescent X-ray analyzer also comprises an F-PC (a first detector) 8A for measuring the intensity of at least a portion of the secondary X-ray 7 which has been monochromatized by the monochromator 6 while allowing the remaining portion of the secondary X-ray 7 to pass therethrough, a light receiving slit member 11 through which the secondary X-ray, which has been monochromatized by the monochromator 6, passes, and a SC (a second detector) 8B for measuring the intensity of the secondary X-ray 7 which has passed through the F-PC 8A or the light receiving slit member 11. The light receiving slit member 11 employed in the practice of the present invention includes two slit elements 11A and 11B. The light receiving slit element 11A is of a type generally utilized in any fluorescent X-ray analyzer of the kind to which the present invention pertains, whereas the light receiving slit element 11B is of a type associated with a low-energy secondary X-ray 7, having a lower resolving power than that of the light receiving slit element 11A, and having a smaller attenuation than that of the light receiving slit element 11A.

Referring to FIG. 1 showing an important portion of the fluorescent X-ray analyzer, the optical path switching device employed in the fluorescent X-ray analyzer comprises a first spindle 14 having the monochromator 6 fixedly mounted thereon with its longitudinal axis O passing across and in touch with a light receiving surface (a lower surface) of the monochromator 6, and a first drive mechanism 15 for driving the first spindle 14. The first spindle 14 is in the form of a quill spindle having its longitudinal axis O coaxial with and concurrently occupied by a second solid spindle 17 as will be described later and is supported by a bearing (not shown) for rotation about the longitudinal axis O independently of and relative to the second spindle 17. The monochromator 6 is fitted to one of opposite ends of the first spindle 14 by means of a generally U-shaped support member 16 with the light receiving surface of the monochromator 6 touching the longitudinal axis O.

The first drive mechanism 15 comprises a stepper motor 15a having a drive shaft and fixedly mounted directly or indirectly on a machine bench (not shown), a worm gear 15b mounted on the drive shaft of the stepper motor 15a for rotation together therewith, and a helical gear 15c coaxially fixed to an end face of the other of the opposite ends of the first spindle 14 and drivingly meshed with the worm gear 15b.

The optical path switching device also comprises the second spindle 17, which is a solid spindle having a longitudinal axis coaxially aligned with and, hence, common to the longitudinal axis O of the first spindle 14 and which carried the F-PC 8A and the light receiving slit elements 11A and 11B that are arranged in side-by-side relation in a direction circumferentially with respect to the longitudinal axis O, and a second drive mechanism 18 for rotating the second spindle 17. Specifically, the F-PC 8A and the light receiving slit elements 11A and 11B are fixedly mounted on a generally sector-shaped carrier plate 19 which is in turn fixedly mounted on one of the opposite ends of the second spindle 17 which extends through the first spindle 14 through a bearing in a fashion parallel to an axially extending body of the generally U-shaped support member 16. Although not show, the other of the opposite ends of the second spindle 17 is rotatably supported by a portion of the machine bench through a suitable bearing.

The second drive mechanism 18 comprises a stepper motor 18a having a drive shaft and fixedly mounted directly or indirectly on the machine bench (not shown), a worm gear 18b mounted on the drive shaft of the stepper motor 18a for rotation together therewith, and a helical gear 18c fixedly mounted on the second spindle 17 at a location on one side of the helical gear 15c remote from the sector-shaped carrier plate 19 and drivingly meshed with the worm gear 18b.

Figure 2:
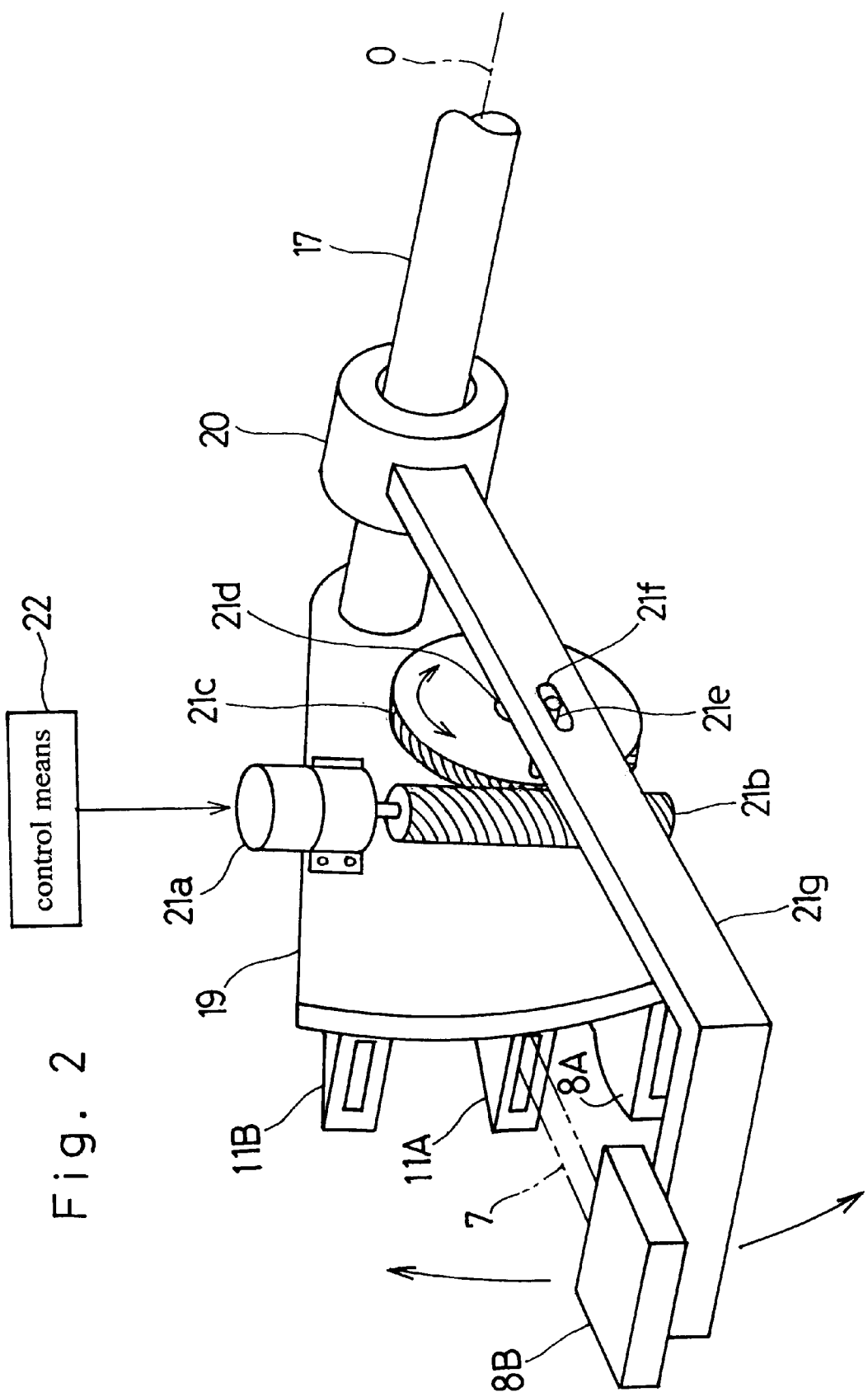
FIG. 2 is a perspective view showing a portion of the path switching device as viewed in a direction shown by A in FIG. 1.
Figure 3:
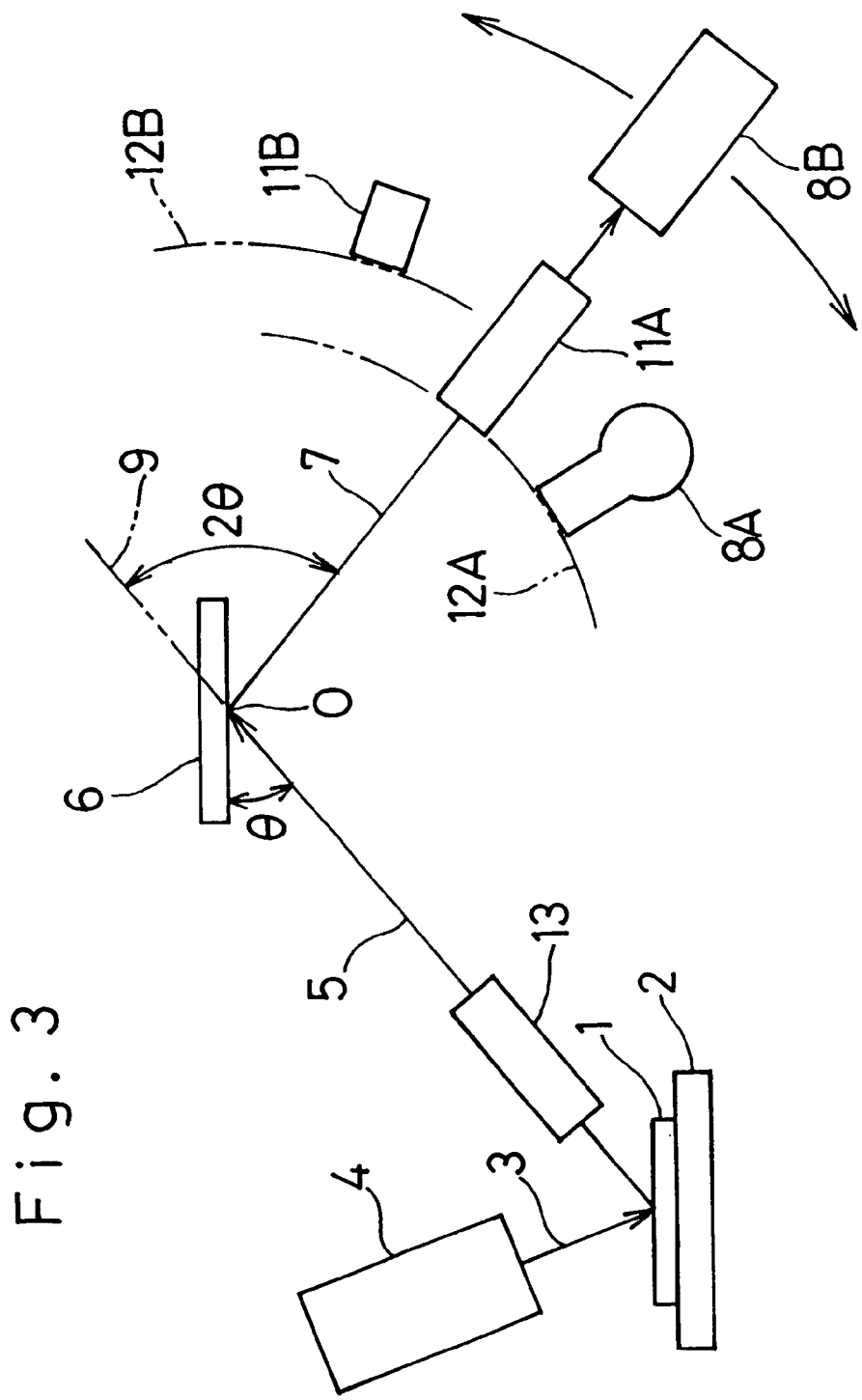
FIG. 3 is a schematic front view showing the fluorescent X-ray analyzer according to the present invention.
Figure 4:
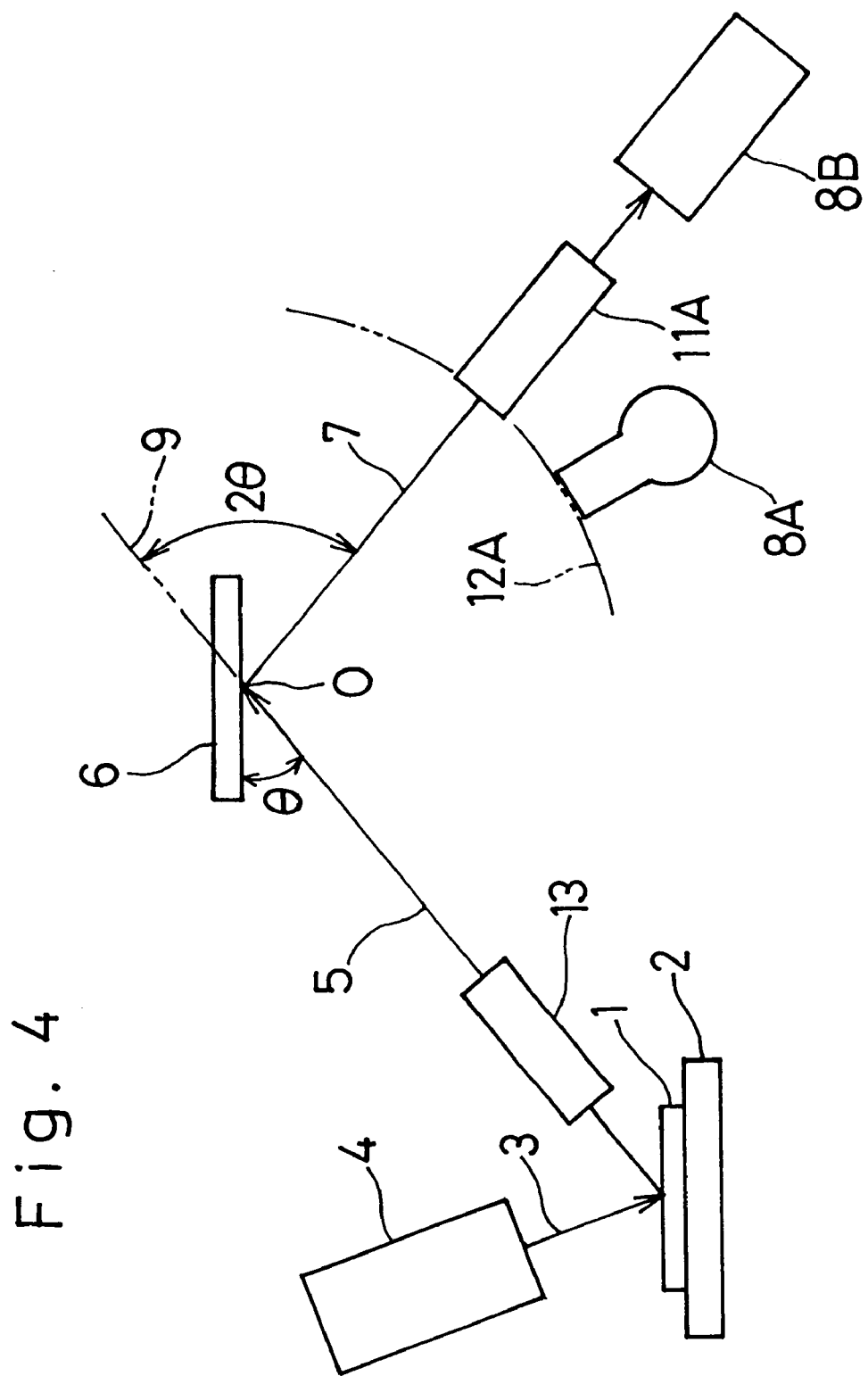
FIG. 4 is a schematic front view showing the prior art fluorescent X-ray analyzer.

The optical path switching device furthermore comprises a third spindle 20 having its longitudinal axis coaxial with and, hence, common to the longitudinal axis O of the first spindle 14 and carrying the SC 8B, and a third drive mechanism 21, shown in FIG. 2, for driving the third spindle 20. The third spindle 20 is in the form of a quill spindle having a longitudinal axis common to the longitudinal axis O together with the second solid spindle 17 and mounted on the second spindle 17 through a bearing (not shown) for rotation independently of and relative to the second spindle 17. The SC 8B is fixedly mounted on a generally L-shaped arm 21g which is in turn fixedly connected to the third spindle 20 so as to extend radially outwardly therefrom.

As clearly shown in FIG. 2, the third drive mechanism 21 comprises a stepper motor 21a having a drive shaft, a worm gear 21b mounted on the drive shaft of the stepper motor 21a for rotation together therewith, and a helical gear 21c drivingly meshed with the worm gear 21b. The helical gear 21c has a connecting pin 21e rigidly connected thereto so as to extend laterally in a direction parallel to the axis of rotation of the helical gear 21c and loosely engaged in a slot 21f defined in the arm 21g.

The third drive mechanism 21 of the structure described above is carried by the second spindle 17 in a manner which will now be described. As best shown in FIG. 2, the stepper motor 21a having its drive shaft on which the worm gear 21b is fixedly mounted is fixedly carried by the sector-shaped carrier plate 19 which is in turn fixed on the second spindle 17, and the helical gear 21c of the third drive mechanism 21 is rotatably mounted on a support spindle 21d secured to the sector-shaped carrier plate 19 rigid with the second spindle 17. Thus, it will readily be seen that not only can the helical gear 21c of the third drive mechanism 21 be rotated about the carrier spindle 21d rigid with the sector-shaped carrier plate 19 when the worm gear 21b is driven by the stepper motor 21a, but also the helical gear 21c together with the worm gear 21b and the stepper motor 21a can be turned about the longitudinal axis O when the second spindle 17 is driven by the stepper motor 18a through the worm gear 18b drivingly meshed with the helical gear 18c.

The L-shaped arm 21g carrying the SC 8B is operatively coupled with the helical gear 21c through the connecting pin 21e loosely engaged in the slot 21f in such arm 21g. Accordingly, the helical gear 21c and the connecting pin 21e altogether constitute a cranking mechanism that permits the arm 21g and, hence, the third spindle 20 to turn about the second spindle 17 as the helical gear 21c is rotated about the carrier spindle 21d and, hence, about the longitudinal axis O by the worm gear 21b during activation of the stepper motor 21a. It is to be noted that the SC 8B carried by the arm 21g as hereinbefore described is positioned on one end of the arm 21g remote from the third spindle 20.

The third drive mechanism 21 may not be always limited to the structure described above, but may comprises a helical gear directly and coaxially mounted on the third spindle so that such helical gear can be driven in mesh with the work gear 21b.

As best shown in FIG. 1, the optical path switching device comprises a control means 22 for controlling the first and second drive mechanisms 15 and 18 so as to allow the wavelength of the secondary X-ray 7 incident upon the F-PC 8A or any one of the light receiving slit elements 11A and 11B to vary and, also, the third drive mechanism 21 (FIG. 2) to allow the secondary X-ray 7, which has passed through the F-PC 8A or any one of the light receiving slit elements 11A and 11B, to be incident upon the SC 8B. More specifically, the control means 22 controls respective rotations of the stepper motors 15a, 18a and 21a.

The operation of the fluorescent X-ray analyzer of the present invention will now be described. As shown in FIG. 3, the fluorescent X-ray analyzer embodying the present invention includes a first optical detection path extending from the monochromator to the SC 8B via the light receiving slit element 11A, a second optical detection path extending from the monochromator 6 to the SC 8B via the light receiving slit element 11B, a third optical detection path extending from the monochromator 6 to the SC 8B via the F-PC 8A, and a fourth optical detection path extending from the monochromator 6 to the F-PC 8A. The optical path switching device hereinbefore described enables a selection of one of the first to fourth optical detection paths. More specifically, when the intensity of the secondary X-ray 7 of a sufficiently high energy is desired to be measured, an external instruction must be given to the control means 22, shown in FIG. 2, through an input means (not shown) to acknowledge that the first optical detection path is utilized. In response to this instruction, the control means 22 performs the following control operation.

In the first place, the stepper motor 21a of the third drive mechanism 21 is properly driven to position the SC 8B at a location rearwardly of the light receiving slit element 11A as shown in FIG. 2. This condition is maintained unless the stepper motor 21a is again driven. Then, the stepper motors 15a and 18a of the first and second drive mechanisms 15 and 18 are properly driven to bring the monochromator 6 and both of the light receiving slit element 11A and the SC 8A to a predetermined start position, respectively.

Starting from this condition, the sample piece 1 fixed on the sample table 2 is irradiated by the primary X-ray 3 from the X-ray source 4 to excite the sample piece 1. As a result of excitation, the sample piece 1 generates the secondary X-ray 5 which is, after having passed through the divergent slit 13, monochromatized by the monochromator 6 so that the SC 8B can measure the intensity of the fluorescent X-ray 7 which has been monochromatized and subsequently passed through the light receiving slit element 11A. In this way, the fluorescent X-ray generated from the sample piece 1 can be analyzed in a sufficiently high energy range. At this time, in order to allow the wavelength of the secondary X-ray 7 incident upon the light receiving slit element 11A to vary, respective drives of the respective stepper motors 15a and 18a (FIG. 1) of the first and second drive mechanisms 15 and 18 are controlled.

In other words, when the secondary X-ray 5 is impinge upon the monochromator 6 at a certain angle of incidence θ, an extension 9 of the path of travel of the primary X-ray 5 and the secondary X-ray 7 that has been monochromatized by the monochromator 6 form an angle of diffraction 2θ which is twice the angle of incidence θ. However, the control means 22 shown in FIG. 1 controls the first and second drive mechanisms 15 and 18 to properly drive the associated stepper motors 15a and 18a to cause the monochromator 6 to be turned about the axis O, passing through the center of the light receiving surface of the monochromator 6 and lying perpendicular to the plane of the drawing, accompanied by turning of the light receiving slit element 11A and the SC 8B along the circular path 12A about the axis O through an angle equal to twice the angle of rotation of the monochromator 6, whereby the angle of diffraction 2 can be varied to change the wavelength of the secondary X-ray 7 being then monochromatized and, also, the monochromatized secondary X-ray 7 can continue to impinge upon the SC 8B through the light receiving slit element 11A.

On the other hand, where the intensity of the secondary X-ray 7 having a low energy is desired to be measured, one of the second to fourth optical detection paths has to be selected depending on the intensity of the secondary X-ray 7. For this purpose, an external instruction descriptive of selection of one of the second to fourth optical detection paths has to be inputted to the control means 22 shown in FIG. 2 through an input means (not shown). In response to the external instruction, the control means 22 causes the stepper motor 21a of the third drive mechanism 21 to be properly driven so that, where the second optical detection path is selected, the SC 8B can be positioned rearwardly of the light receiving slit element 11B; where the third optical detection path is selected, the SC 8B can be positioned rearwardly of the F-PC 8A; or where the fourth optical detection path is selected, the SC 8B will not be positioned rearwardly of the F-PC 8A. Thereafter, unless the stepper motor 21a is driven again, the respective condition appropriate to the selected optical detection path can be maintained.

Then, the stepper motors 15a and 18a of the first and second drive mechanisms 15 and 18 shown in FIG. 1 are properly driven to bring to a predetermined start position the monochromator 6 and both of the light receiving slit element 11B and the SC 8B where the second optical detection path is selected, the monochromator and both of the F-PC 8A and the SC 8B where the third optical detection path is selected, or the monochromator 6 and the F-PC 8A where the fourth optical detection path is selected.

Starting from this condition, the sample piece 1 fixed on the sample table 2 is irradiated by the primary X-ray 3 from the X-ray source 4 to excite the sample piece 1. As a result of excitation, the sample piece 1 generates the secondary X-ray 5 which is, after having passed through the divergent slit 13, monochromatized by the monochromator 6 so that the SC 8B can measure the intensity of the fluorescent X-ray 7 which has been monochromatized and subsequently passed through the light receiving slit element 11B, where the second optical detection path is selected; the F-PC 8A and SC 8B can measure the intensity of the fluorescent X-ray 7 which has been monochromatized, where the third optical detection path is selected; or the F-PC 8A can measure the intensity of the fluorescent X-ray 7 which has been monochromatized, where the fourth optical detection path is selected. It is to be noted that causing the F-PC 8A and SC 8B to measure the intensity of the fluorescent X-ray 7 means that a remaining portion of the secondary X-ray 7 which has, even though received by the F-PC 8A, been passed because of an incapability of the F-PC 8A to measure the intensity thereof completely is measured by the SC 8B so that the intensity of the secondary X-ray 7 can be accurately measured by summing the respective intensities of the secondary X-ray 7 measured by F-PC 8A and SC 8B.

Through the measurement by the utilization of a selected one of the first to fourth optical detection paths, the fluorescent X-ray generated from the sample piece 1 can be analyzed in a desired energy range. At this time, the respective stepper motors 15a and 18a (FIG. 1) of the first and second drive mechanisms 15 and 18 are controlled in a manner similar to that effected when the first optical detection path is selected, so that the wavelength of the secondary X-ray 7 incident upon the light receiving slit element 11B can be varied where the second optical detection path is selected, or the wavelength of the secondary X-ray 7 incident upon the F-PC 8A can be varied where the third or fourth optical detection path is selected. It is, however, to be noted that the light receiving slit elements 11A and 11B and the F-PC 8A need not be turned along the same circular path 12A and, instead, the light receiving slit element 11B, for example, may be turned along a circular path 12B different in diameter from, but coaxial with the circular path 12A.

As hereinbefore fully described, according to the optical path switching device of the present invention, as shown in FIG. 1, since the SC 8B is carried by the third spindle 20 which is different and independent from the second spindle 17 by which the F-PC 8A and both of the light receiving slit elements 11A and 11B are carried in the form as arranged in side-by-side relation with each other in the circumferential direction, one of the first to fourth optical detection paths can be selected. Also, owing to the use of the cranking mechanism comprised of the helical gear 21c and the connecting pin 21e, and the L-shaped arm 21g, the third drive mechanism 21 can be assembled in a compact size.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, the third drive mechanism 21 may be mounted on the machine bench independently of the second spindle, and the control means may be of any suitable design provided that it can control the third drive mechanism 21 in such a way as to cause the secondary X-ray 7, which has passed through the first detector or the light receiving slit, to impinge upon the second detector.

Also, the first detector may not be always limited to the F-PC 8A such as shown and described, but may be a sealed proportional counter tube and, similarly, the second detector may not be always limited to the SC 8B such as shown and described, but may be a sealed proportional counter tube.

In addition, the number of the light receiving slit member may not be limited to two, i.e., the light receiving slit elements 11A and 11B such as shown and described, but may be one or three or more.

Furthermore, the analyzer may be of a design employing a plurality of monochromators which can be selectively utilized one at a time depending on the wavelength (energy) of the secondary X-ray to be measured.

Accordingly, such changes and modifications are, unless they depart from the scope of the present invention as delivered from the claims annexed hereto, to be construed as included therein.

What is claimed is:

1. A fluorescent X-ray analyzer which comprises:

a sample bench for support thereon of a sample piece;

an X-ray source for radiating a primary X-ray towards the sample piece on the sample bench;

a monochromator for monochromatizing a secondary X-ray emitted from the sample piece;

a first detector for measuring an intensity of at least a portion of the secondary X-ray monochromatized by the monochromator while allowing the remaining portion of the secondary X-ray to pass therethrough;

a light receiving slit member operable to pass therethrough the secondary X-ray which has been monochromatized by the monochromator;

a second detector for measuring an intensity of the secondary X-ray which has been passed through the first detector or the light receiving slit member;

a first spindle having a longitudinal axis and carrying the monochromator with the longitudinal axis thereof passing in touch with a light receiving surface of the monochromator;

a first drive mechanism for driving the first spindle;

a second spindle having a longitudinal axis coaxial and common with the longitudinal axis of the first spindle and carrying the first detector and the light receiving slit member in a side-by-side fashion;

a second drive mechanism for driving the second spindle;

a third spindle having a longitudinal axis coaxial and common with the longitudinal axis of the first spindle and carrying the second detector;

a third drive mechanism for driving the third spindle; and a control means for controlling the first and second drive mechanisms to vary a wavelength of the secondary X-ray incident upon the first detector or the light receiving slit member and for controlling the third drive mechanism to cause the secondary X-ray, having passed through the first detector or the light receiving member, to impinge upon the second detector.

2. The fluorescent X-ray analyzer as claimed in claim 1, wherein the third drive mechanism is mounted on the second spindle.

3. The fluorescent X-ray analyzer as claimed in claim 2, wherein the third drive mechanism comprises:

a cranking member rotatable about an axis fixed relative to the second spindle; and a rocking arm having one of opposite ends thereof fixed to the third spindle and capable of being rocked about the longitudinal axis of the third spindle by the cranking member, and wherein the second detector is disposed at a location spaced from such one of the opposite ends of the rocking arm.

4. The fluorescent X-ray analyzer as claimed in any one of claims 1 to 3, wherein the first drive mechanism comprises a stepper motor having a drive shaft, a worm gear mounted on the drive shaft of the stepper motor for rotation together therewith, and a helical gear fixedly mounted on the first spindle and drivingly meshed with the worm gear.

5. The fluorescent X-ray analyzer as claimed in any one of claims 1 to 3, wherein the second drive mechanism comprises a stepper motor having a drive shaft, a worm gear mounted on the drive shaft of the stepper motor for rotation together therewith, and a helical gear fixedly mounted on the second spindle and drivingly meshed with the worm gear.

6. The fluorescent X-ray analyzer as claimed in claim 3, wherein the arm has a slot defined therein, and wherein the third drive mechanism comprises a stepper motor having a drive shaft, a worm gear mounted on the drive shaft of the stepper motor for rotation together therewith, a helical gear drivingly meshed with the worm gear, and the arm having a slot in which a connecting pin fixed to the helical gear so as to protrude laterally outwardly from the helical gear is loosely engaged, said cranking member being constituted by the helical gear and the connecting pin.

7. The fluorescent X-ray analyzer as claimed in claim 1, wherein the first detector is one selected from the group consisting of a gas-flow proportional counter tube and a sealed proportional counter tube and the second detector is one selected from the group consisting of a scintillation counter and a sealed proportional counter tube.

8. The fluorescent X-ray analyzer as claimed in claim 1, wherein the light receiving slit member comprises a plurality of light receiving slit elements.

9. The fluorescent X-ray analyzer as claimed in any one of claims 2, 3, or 6, in which the first detector is one selected from the group consisting of a gas-flow proportional counter tube and a sealed proportional counter tube and the second detector is one selected from the group consisting of a scintillation counter and a sealed proportional counter tube.

10. The fluorescent X-ray analyzer as claimed in any one of claims 2, 3, 6 or 7, in which the light receiving slit member comprises a plurality of light receiving slit elements.

* * * * *